United States Patent [19]
Powles et al.

[11] Patent Number: 5,330,443
[45] Date of Patent: Jul. 19, 1994

[54] ASPIRATION NEEDLE, SYRINGE FOR USE THEREWITH, APPARATUS INCORPORATING THE SAME AND KIT FOR USE IN FINE NEEDLE ASPIRATION CYTOLOGY

[76] Inventors: Trevor J. Powles, Greenhedges, Coulsdon Lane, Chipstad, Surrey, CR55QP, United Kingdom; Mir A. Imran, 731 Barron Dr., Palo Alto, Calif. 94306

[21] Appl. No.: 49,998

[22] Filed: Apr. 20, 1993

[51] Int. Cl.⁵ .................. A61M 5/00; A61M 5/31
[52] U.S. Cl. .................. 604/240; 604/272; 128/763; 128/770
[58] Field of Search .................. 604/272–274, 604/239, 187, 264, 51, 240, 243, 247; 128/763, 770, 751

[56] References Cited

U.S. PATENT DOCUMENTS

| | | | |
|---|---|---|---|
| 4,391,274 | 7/1983 | Kagan | 604/190 |
| 4,581,024 | 4/1986 | Swenson | 604/240 |
| 4,834,722 | 5/1989 | Zenz | 604/272 |
| 5,017,191 | 5/1991 | Yamada et al. | 604/243 |

FOREIGN PATENT DOCUMENTS

| | | | |
|---|---|---|---|
| 2632190 | 12/1989 | France | 604/110 |
| 0706150 | 3/1954 | United Kingdom | 604/272 |
| 2081231 | 2/1982 | United Kingdom | 604/239 |

OTHER PUBLICATIONS

"Technology Report: The Importance of Interior Surface Finish"; National Needle News, vol. 1, No. 2, Apr. 1993, p. 2.

Primary Examiner—C. Fred Rosenbaum
Assistant Examiner—V. Alexander
Attorney, Agent, or Firm—Flehr, Hohbach, Test, Albritton & Herbert

[57] ABSTRACT

An aspiration needle for use with a syringe for fine needle aspiration cytology comprising a rigid elongate tubular member having distal and proximal extremities. The distal extremity is formed to provide a sharp point. The tubular member has a bore extending therethrough from the distal extremity to the proximal extremity. A body is secured to the proximal extremity of the tubular member and forms a chamber therein in communication with the bore of the tubular member. The chamber is formed by a sloping uninterrupted side wall leading to the bore of the tubular member. The body includes a fitting for receiving the syringe and for establishing communication between the syringe and the chamber.

6 Claims, 2 Drawing Sheets

ASPIRATION NEEDLE, SYRINGE FOR USE THEREWITH, APPARATUS INCORPORATING THE SAME AND KIT FOR USE IN FINE NEEDLE ASPIRATION CYTOLOGY

This invention relates to an aspiration needle, a syringe for use therewith, apparatus incorporating the same and kit for use in fine needle aspiration cytology.

Fine needle aspiration cytology has heretofore been utilized as a standard technique for the diagnosis of cancer utilizing a standard 23 gauge intravenous needle attached to a standard 10 milliliter syringe. In such a technique, the intravenous needle is passed through the skin into the tumor. The barrel of the syringe is withdrawn 3 or 4 milliliters while attached to the needle as the needle is passed three or four times through the tumor. This procedure sucks up a small amount of tissue fluid together with loose cells into the needle with some concurrent spillage up into the nozzle of the syringe. The needle is then removed from the tumor and detached from the syringe. Air is then drawn up into the syringe. The needle is reattached and the small amount of fluid with cells therein in the needle is forced out of the needle by operation of the syringe and blown onto a microscopic slide. The small amount of fluid is then smeared against another slide to produce a film on both slides which is then air dried and appropriately stained. Typically an accurate analysis of the lump can be made from a microscopic examination of these slides by an expert. In such a procedure it has been found that with a standard 23 gauge needle, the volume of the needle is often exceeded by the aspirate so that the sample passes up into the socket of the needle connected to the syringe and is partly entrapped therein preventing expression of the sample onto the slide. Also, it has been found that in many cases, the sample so obtained is inadequate to provide a clear diagnosis. Furthermore, newly developed immunocytochemical techniques for detecting proteins in cells can be used on cytological preparations for predicting growth characteristics, prognosis and likely response to treatment. These techniques require larger numbers of cells, than are currently obtained using standard aspiration equipment. Utilizing such standard intravenous needles, it has only been possible to obtain something in the order of 5,000–10,000 cells which is only adequate for a immunocytochemical use in about 60-70% of the patients. There is therefore need for a new and improved aspiration needle which will make it possible to obtain larger cell samples without increasing the external size of the needle. In addition, it has been found that the syringes utilized with such aspiration needles have been difficult to use during such aspiration procedures. There is therefore also a need for a new and improved syringe for use with the improved aspiration needle.

In general, it is an object of the present invention to provide an aspiration needle, a syringe for use therewith, an apparatus incorporating the same and a kit for use in fine needle aspiration cytology.

Another object of the invention is to provide an aspiration needle of the above character in which larger cell samples can be obtained without increasing the outside diameter of the needle.

Another object of the invention is to provide an aspiration needle of the above character in which aspirated cells do not become entrapped in the aspiration needle.

Another object of the invention is to provide an aspiration needle of the above character which is made in a small size so as to cause as little discomfort as possible to the patient.

Another object of the invention is to provide an aspiration needle of the above character which is sized so as to minimize bleeding and damage around the tumor and to inhibit disturbing the integrity of the tumor.

Another object of the invention is to provide an aspiration needle of the above character which has the necessary column strength to penetrate skin soft tissues and the tumor.

Another object of the invention is to provide an aspiration needle of the above character which can be readily manufactured.

Another objective of the invention is to provide an aspiration needle of the above character to provide larger cell samples for preparing adequate cell suspensions for use in immunocytochemical techniques.

Another object of the invention is to provide a syringe which can be utilized with the aspiration needle which is easy to operate.

Another object of the invention is to provide a syringe of the above character in which air can be introduced into the syringe without removing the syringe from the aspiration needle.

Another object of the invention is to provide an apparatus of the above character in which the vacuum for the aspiration needle is provided by a foot operated mechanism.

Another object of the invention is to provide a kit which includes a aspiration needle, a syringe for use therewith and a sealed sterile vial containing a chemically defined medium so that the kit provides all that is required for a cancer screening operation using fine needle aspiration cytology.

Additional objects and features of the invention will appear from the following description in which the preferred embodiments are set forth in detail in conjunction with the accompanying drawings.

In general, the aspiration needle incorporating the present invention for use with a syringe for fine needle aspiration cytology is comprised of a rigid elongate tubular member having distal and proximal extremities. The distal extremity is formed to provide a sharp point. The tubular member has a bore extending therethrough from the distal extremity to the proximal extremity. A body is secured to the proximal extremity of the tubular member and forms a chamber which is in communication with the bore of the tubular member. The chamber is formed by a sloping continuous uninterrupted side wall leading to the bore of the tubular member. The body secured to the proximal extremity of the tubular member includes means for receiving the syringe and for establishing communication between the syringe and the chamber.

Figure 2:
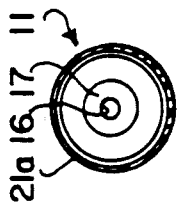
FIG. 2 is a cross-sectional view taken along the line 2—2 of FIG. 1.
Figure 4:
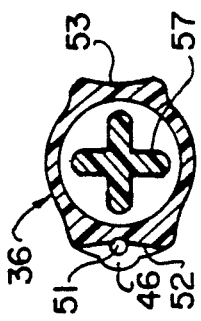
FIG. 4 is a cross-sectional view taken along the line 4—4 of FIG. 3.
Figure 5:
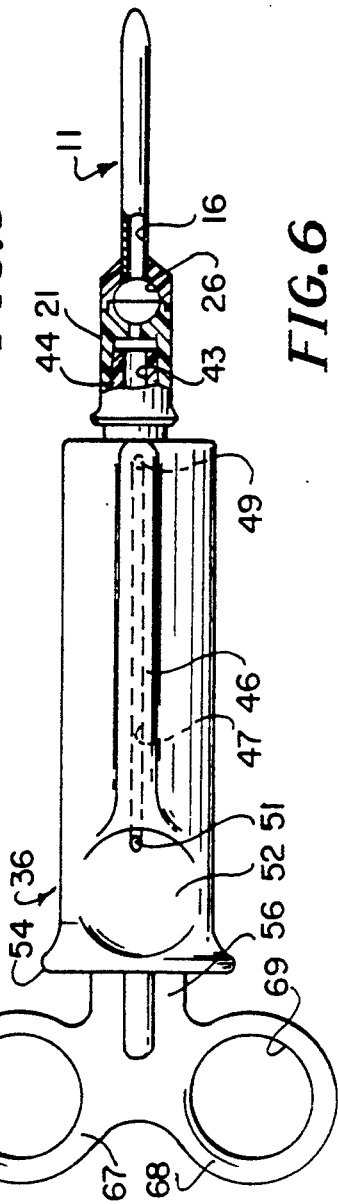
FIG. 5 is a cross-sectional view taken along the line 5—5 of FIG. 3.
Figure 1:
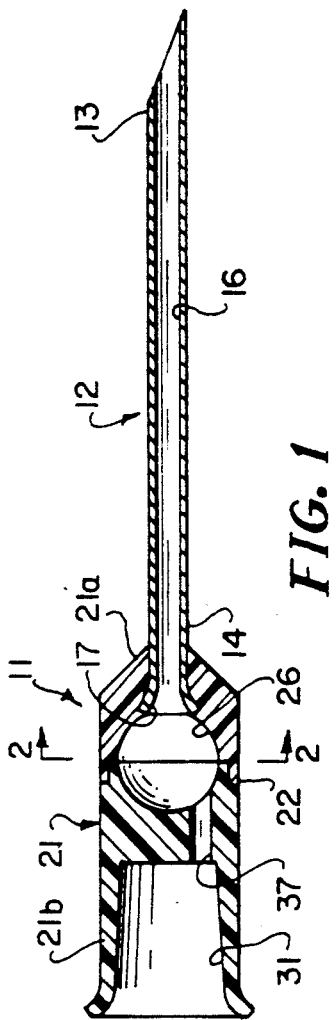
FIG. 1 is a side-elevational view in cross section of an aspiration needle incorporating the present invention.
Figure 3:
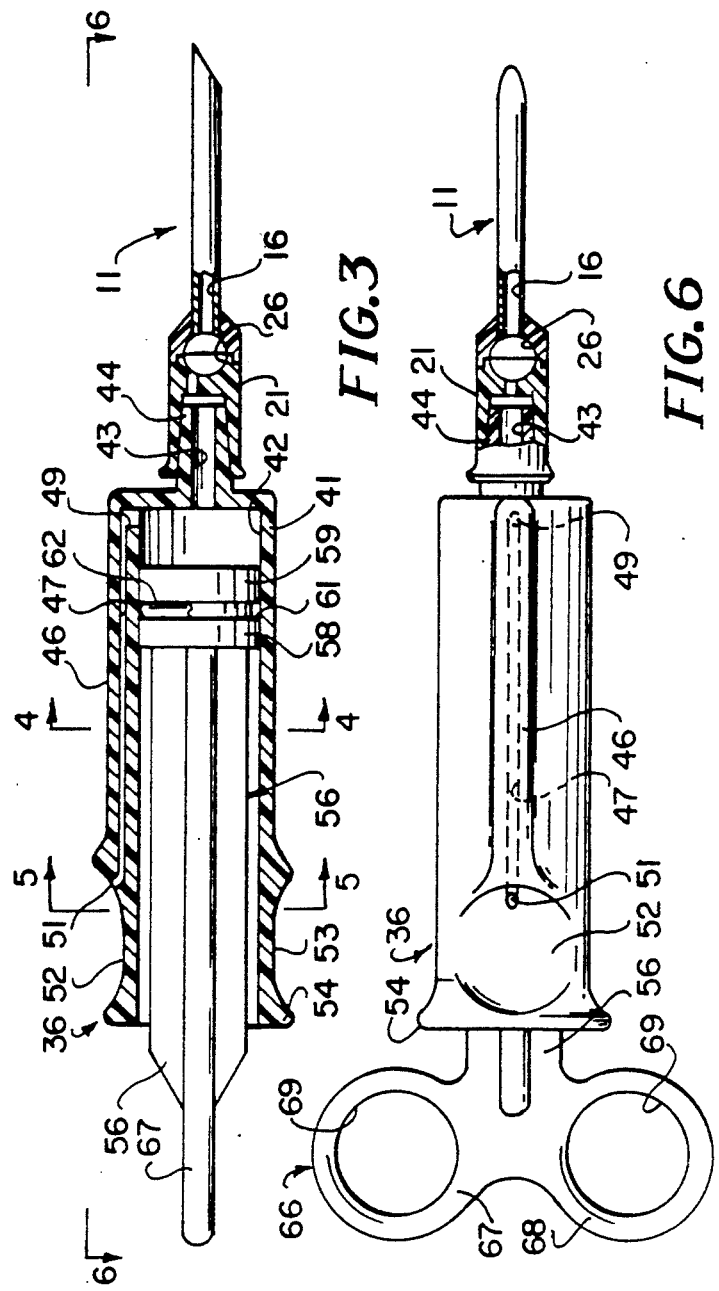
FIG. 3 is a side-elevational view in cross section of a syringe incorporating the present invention mounted on the aspiration needle shown in FIG. 1.
Figure 6:
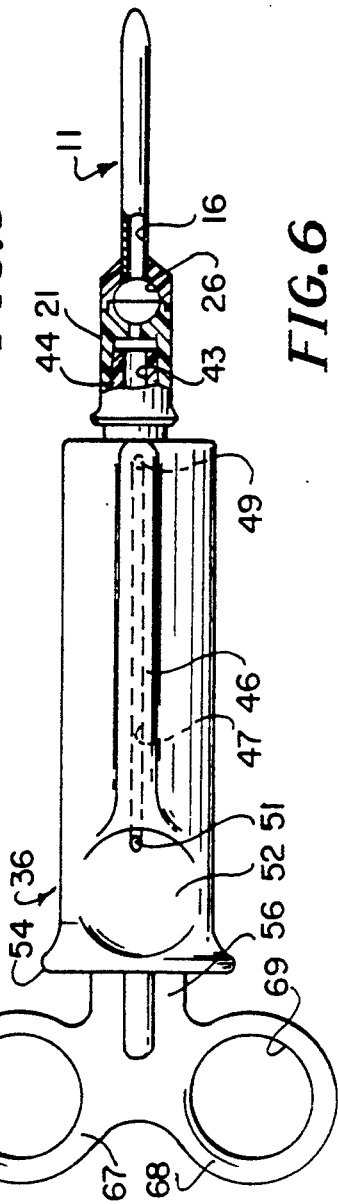
FIG. 6 is a side-elevational view taken along the line 6—6 of FIG. 3.

More particularly, the aspiration needle 11 which is shown in FIGS. 1 and 2 consists of a rigid elongate tubular member 12 formed of a suitable material such as stainless steel. The tubular member 12 should have a suitable length so that it can reach tumors as hereinafter described. Typically the tubular member should have a length ranging from 2 to 8 centimeters. The tubular member can have an external diameter corresponding to the size of a 23 gage needle. For example it can have an outside diameter of approximately 0.025 inches with an inside diameter ranging from 0.018–0.020 inches to provide a wall thickness ranging from 0.0025 inches to 0.003 inches to provide the desired column strength for the needle. The tubular member 12 is provided with distal and proximal extremities 13 and 14. The distal extremity 13 is formed to provide a point, as for example by sharpening the same in the form of an inclined wedge as shown in FIG. 1. The tubular member is provided with a bore 16 which extends from the distal extremity 13 to the proximal extremity 14. As shown in FIG. 1, the proximal extremity 14 of the tubular member 12 can be flared outwardly to provide a funnel-shaped recess 17 leading into the bore 16. It has been found that by providing a tubular member having such a wall thickness it is still possible to achieve the necessary column strength for the tubular member so that the needle can be introduced into the tissue that it is desired to penetrate.

A body 21 formed of a suitable transparent material such as ULTEM is mounted on the proximal extremity 14. The body 21 by way of example can be formed in two parts 21a and 21b which are joined together at a joint 22 formed by cooperating annular recesses and flanges joined together by suitable means such as ultrasonic bonding. The body 21 can have a generally cylindrical configuration and has formed therein a chamber 26 which is shown as being generally spherical which is in communication with the funnel-shaped passage 17 and the bore 16. The chamber 26 is formed by a wall of the body that has a highly polished surface and is sloping and uninterrupted leading into the funnel-shaped passage 17 and provides a smooth transition with no interruptions between the wall forming the chamber 26 and the flanged proximal extremity 14 of the tubular member 12.

The chamber 26 can be of a suitable size, as for example from 0.075 milliliters to 0.15 milliliters and preferably approximately 0.1 milliliters. As can be seen, the joint 22 extends across the chamber 26 to permit ready access to the chamber so that the tubular member 12 with its swaged proximal extremity 14 can be readily mounted in the part 21a. This also makes it possible to ensure that there are highly polished surfaces in the chamber and that there is an uninterrupted sloping wall leading into the funnel-shaped passage 17.

The part 21b of the body 21 serves as a hub and has a tapered circular recess 31 which is adapted to receive a conventional syringe or a syringe 36 incorporating the present invention of the type shown in FIGS. 3–6. The body 21 is provided with a small bore 37 offset to one side of the recess 31 which extends from the tapered recess 31 into the chamber 26.

The syringe 36 consists of a barrel 41 formed of a suitable material such as plastic. As shown, it is generally cylindrical in shape and is provided with an inner cylindrical recess or chamber 42 which is in communication with a bore 43 provided in a tubular extension 44 of the barrel 41. The barrel 41 is provided with an elongate protrusion 46 formed integral therewith which extends longitudinally of the barrel 41 and has a bore 47 extending along the length thereof with the distal extremity being in communication with a hole 49 entering into the cylindrical chamber 42. The proximal extremity of the bore 47 opens through a hole 51 which is disposed in the distal extremity of a finger-shaped recess 52 provided in the barrel near the proximal extremity of the barrel 41 for grasping by the middle finger. A thumb-shaped recess 53 is also formed in the barrel 41 generally opposite the recess 52. The proximal extremity of the barrel 41 is provided with an outwardly extending annular lip 53 which is adjacent the recesses 52 and 53.

The syringe 36 also includes a plunger 56 which is slidably mounted within the chamber 42 and consists of a cross-shaped member 57 (see FIG. 4) having first and second radially extending flanges 58 and 59 provided on the distal extremity of the plunger 86 to form an annular recess 61 in which an o-ring 62 is disposed. A handle 66 is provided on the proximal extremity of the plunger 56 and is formed integral therewith and consists of a pair of finger rings 67 and 68 which lie in a plane and which are disposed adjacent to each other. The rings 67 and 68 are provided with finger-sizes openings 69 through which the fingers of the human hand can extend.

Figure 7:
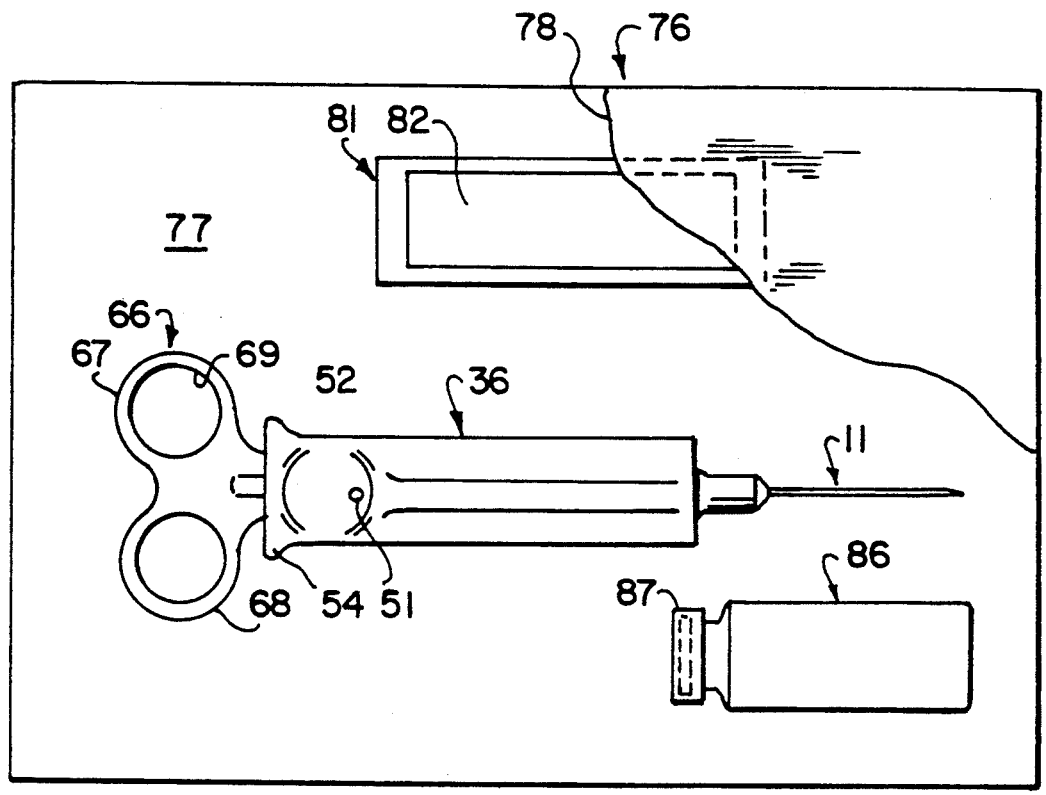
FIG. 7 is a schematic illustration of a foot-operated apparatus incorporating the present invention for use in fine needle aspiration cytology.

Operation and use of the aspiration needle 11 and the syringe 36 can now be briefly described as follows. Let it now be assumed that it is desired to perform a fine needle aspiration cytodiagnosis to provide an accurate nonsurgical diagnosis of a lump which has been found by palpation or other means in a human body such as in a female breast. Let it also be assumed that the surgeon has available an aspiration needle 11 and a syringe 36 incorporating the present invention which has been incorporated into a kit such as shown in FIG. 7 which can be in the form of a blister pack 76 in the form of a cardboard back 77 with an overlying transparent plastic wrap 78. In the blister pack 76 in addition to the syringe 36 and the aspiration needle 11 there is provided a slide carrier or holder 81 which contains a plurality of prepared glass slides 82 of a conventional type, as for example two or three slides which may have been coated with lysine in preparation for dry smears.

Also enclosed in the kit 76 is a bottle or vial 86 which is provided with a cap 87 having a central portion 88 of a conventional type which can be penetrated by the aspiration needle 11. An appropriate chemically defined medium (not shown) is disposed within the hermetically sealed bottle or vial 86 in the form of a liquid with a gaseous atmosphere overlying the liquid. The gaseous atmosphere can be of various types, as for example it can be 100% oxygen to facilitate viability of cancer cells in the medium during transportation of vial 86 to a laboratory.

The surgeon would open such a kit 76 and take out the sterile syringe 36 with the aspiration needle 11 attached thereto and take one of his hands and place the thumb of that hand in the recess 53 and another finger of the hand, as for example the middle finger in the recess 52 and at the same time closing the hole 51. Two other fingers of the same hand as for example the index finger and the ring finger would then be inserted through the finger holes 69. The surgeon using the other hand would locate the palpable breast tumor with the other hand and then would use the hand holding the syringe to introduce the fine aspiration needle 11 through the skin and would direct the needle into the palpable tumor. As soon as it has been assured that the needle has penetrated the tumor, a negative pressure or vacuum can be created within the syringe to aspirate cells and fluid from within the tumor. This can be readily accomplished by the surgeon by withdrawing the plunger 56 with two fingers of the hand while holding a thumb and forefinger in the recesses 52 and 53 to keep the hole 51 closed with the finger to create a subambient condition within the chamber 42 to cause aspirate to be drawn into the bore 16 and the chamber 26 of the needle 11. Since the bore 37 has been offset to one side of the recess 31, there is much less likelihood that aspirate coming through the bore 16 will enter the passage 37 but will all be retained in the bore 16 and the chamber 26.

After the desired amount of aspirate has been withdrawn from the tumor as determined by viewing the presence of aspirate in the chamber 26, the needle 11 can be withdrawn. As soon as the needle 11 has been withdrawn and its distal extremity is exposed to ambient atmospheric pressure, the finger disposed in the recess 52 can be lifted to open the hole 51. Two fingers of the hand can then be utilized to further retract the plunger 56 to draw air into the chamber 42. As soon as sufficient air has been drawn into the chamber 42, the hole 51 is again closed by the middle finger with the middle finger and the thumb grasping the barrel 41 and the index and ring fingers engaging the handle 66 to discharge the air which has been drawn into the chamber 42 to be discharged through the needle 11 to force the aspirate in the chamber 26 and the bore 16. This aspirate can be discharged onto the slides 82 after they have been removed from the slide holder 81. After the aspirate has been discharged onto the slides 82, the slides 82 can be wiped together to form smears on the slides. They can thereafter be air dried and shipped to the laboratory for analysis.

During the same aspiration procedure, a portion of the aspirate or if desired all of the aspirate which has been removed from the tumor can be injected into the medium contained in the hermetically sealed vial 86 by introducing the needle 11 through a central needle penetratable portion 88 provided in the cap 87 and discharging the aspirate into the medium. The syringe can then be withdrawn and the vial 86 can be shipped to the laboratory.

Thus, with such procedures it is possible to prepare slides 82 and the vial 86 so that they carry aspirate for diagnosis by the laboratory. With the syringe 36 hereinbefore described with its air vent, the syringe 36 can be closed off by a finger of the hand. This makes it possible to hold the syringe 36 during the aspiration procedure in a way that retains a sensitivity of feeling where the needle is going while at the same time making it easy to seal off the air vent. Also by providing the air vent in the barrel in the syringe, it is possible to introduce air into the cylindrical chamber 42 without the necessity of separating the syringe 36 from the aspiration needle 11 to thereby readily facilitate the expulsion of the aspirated cells and fluid from the needle 11 onto the slides 82 or into the vial 86.

Typically, a surgeon would utilize the middle finger and the thumb for grasping the barrel by placing the middle finger in the recess 52 and the thumb in the recess 53 and utilizing the index finger and the ring finger for pulling the plunger 56 rearwardly or back. It should be appreciated that if desired, it is possible to provide a plunger with only a handle which can be engaged by a single finger of the hand rather than a handle which permits the use of two fingers of the hand.

The use of the aspiration needle 11 of the present invention is particularly advantageous in that its reduced wall thickness permits larger samples to be obtained with a fine needle no greater in size than those heretofore utilized. Thus sample sizes ranging from 10,000-100,000 cells with a volume of fluid ranging from about 0.05 milliliters to about 0.5 milliliters can be obtained. The provision of the visible chamber 26 ensures that it is possible to obtain adequate samples. Chamber 26 as hereinbefore described is formed in such a manner so as to have very smooth inner surfaces and to have sloping uninterrupted walls so that aspirate cannot be entrapped in the chamber and therefore can be readily expelled from the needle.

Although the use of the aspiration needle 11 and the syringe 36 have been described primarily in connection with the obtaining of aspiration samples from breast tumors, it should be appreciated that the aspiration needle 11 and the syringe 36 can be utilized for obtaining samples from other organs of the human body. For example, such a needle can be utilized for obtaining aspiration samples from the liver. In such a case, the length of the needle should be increased to about 6-8 centimeters with appropriate changes in wall thickness to provide adequate column strength. The aspiration needle has been kept as fine as possible, in other words the small diameter is possible in order to cause as little trauma to the tumor being analyzed as well as little discomfort to the patient as possible. At the same time it is desirable to obtain as large a specimen as possible in such a fine needle by providing a maximum internal diameter within the needle while still maintaining the necessary column strength for the needle to minimize bending or collapse of the needle during the aspiration procedure. By utilizing such a fine needle, it is possible to prevent bleeding and damage around the tumor without disturbing the integrity of the tumor.

Figure 8:
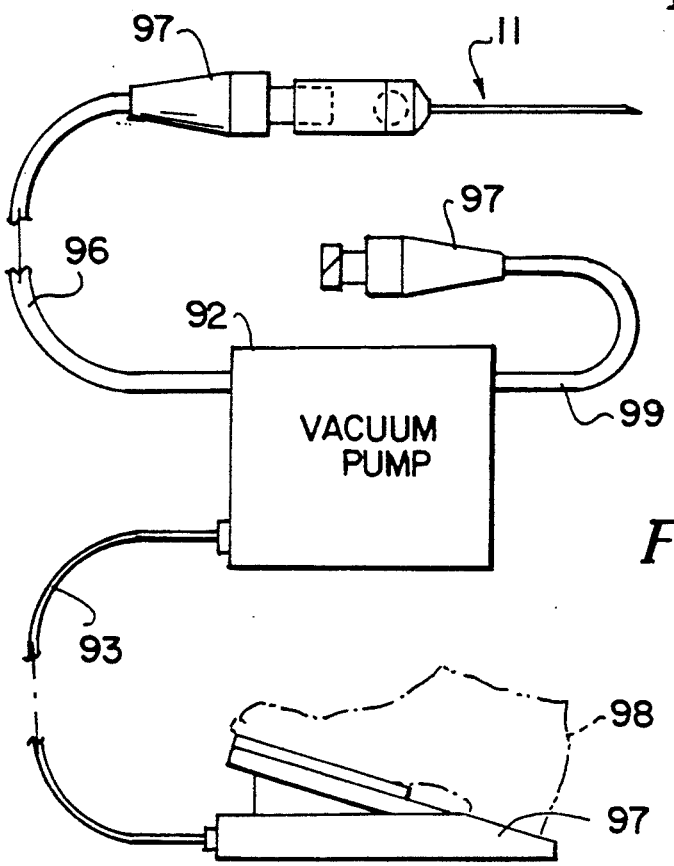
FIG. 8 is a plan view of a kit incorporating the present invention.

Apparatus 91 for utilizing the aspiration needle 11 of the present invention is shown in FIG. 8 and consists of a conventional vacuum pump 92. The vacuum pump 92 can be operated in a suitable manner such as by electric motor (not shown) which is connected by a cord 93 to a foot operated pedal 94 for supplying a subatmospheric or a vacuum condition to a tube 96 which is connected to a fitting 97 that is adapted to be releasably mounted in the tapered recess 31 provided in the needle 11. It should be appreciated that the desired vacuum can also be created by mechanical motion utilizing a foot-operated pump.

Operation and use of the apparatus shown in FIG. 8 may be briefly described as follows. Typically it may be desirable to utilize the apparatus shown in FIG. 8 when it is desired to do aspiration cytology under ultrasonic control making it desirable to utilize the other hand for holding the sonic source. For some operators, the suction pump technique may be preferable to use of a syringe for obtaining adequate aspiration specimens. The foot 98 of the surgeon can then be utilized for operating the foot pedal 94 to supply a vacuum to the aspiration needle 11 at the appropriate time. After the needle 11 has been withdrawn, the vacuum pump 92 can be provided with a control (not shown) which can reverse the vacuum in other words to supply air under pressure through the tube 96 to discharge the aspirate in the needle 11 onto slides 82 or into a vial 86 as hereinbefore described. This would require a 'fail safe' mechanism (not shown) to prevent injection of air into the patients. Alternatively, the vacuum pump 92 can be provided with two tubes, one tube 96 as hereinbefore described supplying a vacuum and the other tube 99 supplying air under pressure. A fail safe device to prevent air under pressure being injected into the patient could be achieved by making the tube 99 too short to reach the patient. Tube 96 having the vacuum would be utilized to withdraw aspirate and the other tube 99 with a similar fitting 97 would be used to discharge the aspirate from the needle 11. A fail safe device would be required to prevent such pressure from being exerted whilst the aspiration needle is in the patient.

From the foregoing it can be seen that there has been provided an aspiration needle and a syringe and apparatus associated therewith and a kit all of which are user friendly and can be utilized for withdrawing relatively large samples of aspirate while retaining the desirable characteristics of fine needle aspirations cytology to minimize disturbance of the tumor and trauma to the patient.

What is claimed is:

1. An aspiration needle for use in collecting larger cell samples with a syringe for fine needle aspiration cytology without increasing the size of the needle comprising a rigid elongate tubular member having distal and proximal extremities, the distal extremity being formed to provide a sharp point, the tubular member having a bore extending therethrough from the distal extremity to the proximal extremity and having an opening at the distal extremity in communication with the bore and a body secured to the proximal extremity of the tubular member and forming a chamber therein in communication with and in close proximity to the opening to the bore of the tubular member, said chamber being formed by a sloping uninterrupted side wall leading distally to the opening to the bore of the tubular member, said body including a hub separate from the chamber and spaced proximally of the chamber for receiving said syringe and for establishing communication between the syringe and the chamber.

2. An aspiration needle as in claim 1 wherein said body is formed of plastic and wherein said tubular member is formed of stainless steel.

3. An aspiration needle as in claim 2 wherein said body is transparent.

4. An aspiration needle as in claim 1 wherein said tubular member has a wall thickness ranging from approximately 0.0025 inches to 0.003 inches.

5. An aspiration needle as in claim 4 wherein said tubular member has an outside diameter of approximately 0.025 inches and less and has an inside diameter ranging from 0.018–0.020 inches.

6. An aspiration needle as in claim 1 wherein said proximal extremity of the tubular member is flared outwardly to provide a funnel-shaped passage to the bore and wherein the chamber in said body forms a smooth transition between the chamber and the funnel-shaped passage to the bore.

* * * * *